United States Patent [19]

Lin et al.

[11] Patent Number: 5,948,855
[45] Date of Patent: Sep. 7, 1999

[54] WATER-IN-OIL-IN WATER EMULSION

[75] Inventors: Zuchen Lin; William James Schulz, Jr.; Shizhong Zhang, all of Midland, Mich.

[73] Assignee: Dow Corning Corporation, Midland, Mich.

[21] Appl. No.: 09/228,863

[22] Filed: Jan. 12, 1999

[51] Int. Cl.$^6$ .............................. C08L 83/00; A61K 6/00
[52] U.S. Cl. ...................... 524/837; 524/588; 424/70.12; 424/401
[58] Field of Search ....................... 524/837, 588

[56] References Cited

U.S. PATENT DOCUMENTS 5,589,177 12/1996 Herb ......................................... 424/401
5,654,362 8/1997 Schulz ...................................... 524/862
5,656,280 8/1997 Herb ......................................... 424/401
5,811,487 9/1998 Schulz ...................................... 524/862

*Primary Examiner*—Morton Foelak
*Attorney, Agent, or Firm*—James L. De Cesare

[57] ABSTRACT

A multiple emulsion of the type $W_1/O/W_2$ is made by first preparing a primary emulsion $W_1/O$ using a silicone fluid as the oil phase (O), and an elastomeric silicone polyether as an emulsifier, for dispersing water phase $W_1$ into oil phase (O). The primary emulsion $W_1/O$ is then added and dispersed into a final continuous water phase $W_2$ to form a multiple emulsion $W_1/O/W_2$. The multiple emulsions are useful for treating the hair, the skin, or the underarm areas of the human body. Vitamins or drugs can be included in the oil phase (O) or in either aqueous phase $W_1$ or $W_2$ to enhance the benefits of the multiple emulsions in personal care applications.

10 Claims, No Drawings

WATER-IN-OIL-IN WATER EMULSION

CROSS-REFERENCE TO RELATED APPLICATIONS

Not applicable.

STATEMENT REGARDING FEDERALLY SPONSORED RESEARCH OR DEVELOPMENT

Not applicable.

REFERENCE TO A MICROFICHE APPENDIX

Not applicable.

FIELD OF THE INVENTION

This invention is directed to a multiple emulsion of the type $W_1/O/W_2$, in which an elastomeric silicone polyether is used to form a primary emulsion $W_1/O$, which primary emulsion is then dispersed into a final continuous phase $W_2$. The elastomeric silicone polyether is present at the interface of the primary dispersed phase $W_1$ and the secondary dispersed phase O. Generally, the elastomeric silicone polyether is the only emulsifier required to form such multiple emulsions.

BACKGROUND OF THE INVENTION

Multiple emulsions are composed of droplets of one liquid dispersed in larger droplets of a second liquid which are then dispersed in a final continuous phase. Generally, the internal droplet phase will be miscible with or identical to the final continuous phase. For example, in a water-in-oil-in-water multiple emulsion W/O/W, the internal and external phases are aqueous.

For a W/O/W system, in which the final continuous phase is aqueous, the primary emulsion is a water-in-oil emulsion W/O, which is then emulsified into the final aqueous phase.

For the purpose of clarity, and in accordance with recognized standards of nomenclature used for W/O/W systems, the aqueous phase of the primary emulsion is designated as $W_1$, and the primary emulsion is designated as $W_1/O$. The primary emulsion $W_1/O$ includes an oil phase which is designated as O. After the primary emulsion $W_1/O$ has been further dispersed in the second aqueous phase designated as $W_2$, the complete multiple emulsion system is designated as $W_1/O/W_2$.

According to conventional wisdom, two surfactants or combinations of surfactants must be employed for forming multiple emulsions. One surfactant is used for preparing the primary emulsion $W_1/O$, while a second surfactant, generally significantly different from the one surfactant, is used in the final step of emulsification to the $W_1/O/W_2$ multiple emulsion. This is for the reason that such multiple emulsion systems involve a great variety of phases and interfaces, and their requirements are such that two stabilizing systems must be employed, i.e., one for each of the oil-water interfaces.

The present invention, in contrast, is a marked departure from such conventional wisdom, and multiple emulsions of the $W_1/O/W_2$ type can be prepared using only a single surfactant.

BRIEF SUMMARY OF THE INVENTION

According to this invention, water-in-silicone oil-in-water ($W_1/O/W_2$) emulsions can be formed by simply shearing and diluting water-in-silicone oil ($W_1/O$) emulsions which have been prepared using an elastomeric silicone polyether as an emulsifier. The resulting $W_1/O/W_2$ multiple emulsions possess enhanced stability over state of the art emulsions of this type, due to the elastomeric nature of the silicone phase of the emulsion.

These emulsions are capable of delivering a number of active ingredients, including other types of silicones, by incorporating the active ingredient(s) in the silicone oil phase of the primary emulsion $W_1/O$. For example, oil-soluble active ingredients such as vitamin A and vitamin E, can be emulsified into the silicone oil phase (O) of the primary emulsion, and the primary emulsion can then be emulsified into the continuous water phase $W_2$ forming the $W_1/O/W_2$ multiple emulsion.

Alternatively, water-soluble active ingredients such as vitamin C can be emulsified into the water phase $W_1$ of the primary emulsion $W_1/O$, and the primary emulsion can then be emulsified into the water continuous phase $W_2$ forming the $W_1/O/W_2$ multiple emulsion.

Such multiple emulsion systems are beneficial as they are capable of protecting sensitive active ingredients such as vitamins from oxidation, while at the same time, enabling the vitamin(s) to be delivered from an aqueous matrix onto a substrate, such as hair, skin, and underarm areas of the human body.

These and other features of the invention will become apparent from a consideration of the detailed description.

BRIEF DESCRIPTION OF THE SEVERAL VIEWS OF THE DRAWING

Not applicable.

DETAILED DESCRIPTION OF THE INVENTION

According to this invention, an elastomeric silicone polyether is used, and it can be prepared generally as depicted below:

Step 1: Incorporation of the Polyether
≡SiH siloxane+mono-alkenyl polyether+Pt catalyst→≡SiH siloxane with polyether groups
Step 2: Gelation
≡SiH siloxane with polyether group+≡SiH siloxane (optional)+α,ω-diene, diyne, or ene-yne+oil+Pt catalyst→gel/elastomer
Step 3: Shearing and Swelling—Optional
gel/elastomer+oil+vitamin/drug→paste
Step 4: Emulsification & Preparation of Primary Emulsion
silicone gel/elastomer/paste+$H_2O$+vitamin/drug+shear→primary emulsion $W_1/O$
Step 5: Preparation of Multiple Emulsion $W_1/O/W_2$
primary emulsion $W_1/O$+$H_2O$+shear→$W_1/O/W_2$ In Step 1, the molar ratio of the nono-alkenyl polyether to the ≡SiH in the ≡SiH siloxane should be between 0.9:1 to 1:12.

In Step 2, the weight ratio of the oil to the weight of the ≡SiH siloxane with polyether groups and the alpha, omega-diene can be from 1:1 to 98:1, but preferably is between 5:1 to 15:1. The equivalent ratio of the ≡SiH in the ≡SiH containing siloxane with polyether groups and the alpha, omega-diene can be from 2:1 to 1:2, but preferably is 1:1.

While Step 2 can include a mixture of various types of compounds, at least one ≡SiH containing siloxane must include a polyether group. For example, one formulation found especially suitable for Step 2 is a mixture containing the following compounds:

Me$_3$SiO(Me$_2$SiO)$_{50}$[MeQSiO]$_4$(MeHSiO)$_5$SiMe$_3$
HSiMe$_2$O(Me$_2$SiO)$_{10}$SiHMe$_2$
Me$_3$SiO(Me$_2$SiO)$_8$(MeHSiO)$_4$SiMe$_3$
1,5-hexadiene, and decamethylcyclopentasiloxane. In these formulas, Me is methyl and Q is —CH$_2$CH$_2$CH$_2$O (CH$_2$CH$_2$O)$_{10}$H.

In Step 3, the silicone paste should contain 80–98 percent by weight of the oil. In Step 4, the weight ratio of water to the silicone paste can be 95:5 to 5:95.

The ≡Si—H siloxane in Step 1 is represented by compounds of the formula R$_3$SiO(R'$_2$SiO)$_a$(R"HSiO)$_b$SiR$_3$ referred to as type A$^1$, and compounds of the formula HR$_2$SiO(R'$_2$SiO)$_c$SiR$_2$H or compounds of the formula HR$_2$SiO(R'$_2$SiO)$_a$(R"HSiO)$_b$SiR$_2$H referred to as type A$^2$, as well as mixtures thereof. In the three formulas, R, R', and R", are alkyl groups with 1–6 carbon atoms; a is 0–250; b is 1–250; and c is 0–250. The molar ratio of compounds A$^2$:A$^1$ is 0:1 to 20:1, preferably is 0:1 to 5:1. In preferred embodiments, compounds of types A$^1$ and A$^2$ are used in the reaction, however, it is possible to successfully conduct the reaction using only compounds of type A$^1$.

The ≡Si—H containing polysiloxane A$^1$ can also comprise an alkylhydrogen cyclosiloxane or an alkylhydrogendialkyl cyclosiloxane copolymer, represented in general by the formula (R'$_2$SiO)$_a$(R"HSiO)$_b$ where R', R", a, and b, are as defined above. Preferably, a is 0–7; and b is 3–10. Some representative compounds are (OSiMeH)$_4$, (OSiMeH)$_3$ (OSiMeC$_6$H$_{13}$), (OSiMeH)$_2$(OSiMeC$_6$H$_{13}$)$_2$, and (OSiMeH)(OSiMeC$_6$H$_{13}$)$_3$, where Me is —CH$_3$.

An unsaturated hydrocarbon is used in Step 2, and the most preferred unsaturated hydrocarbon is an alpha, omega-diene of the formula CH$_2$=CH(CH$_2$)$_d$CH=CH$_2$ where d is 1–20. Some representative examples of suitable alpha, omega-dienes for use herein are 1,4-pentadiene; 1,5-hexadiene; 1,6-heptadiene; 1,7-octadiene; 1,8-nonadiene; 1,9-decadiene; 1,11-dodecadiene; 1,13-tetradecadiene; and 1,19-eicosadiene.

However, other unsaturated hydrocarbons can be used such as alpha, omega-diynes of the formula CH≡C(CH$_2$)$_e$C≡CH; or alpha, omega-ene-ynes of the formula CH$_2$=CH (CH$_2$)$_e$C≡CH where e is 0–20. Some representative examples of suitable alpha, omega-diynes for use herein are 1,3-butadiyne HC≡C—C≡CH and 1,5-hexadiyne (dipropargyl) HC≡C—CH$_2$CH$_2$—C≡CH. One example of a suitable alpha, omega-ene-yne for use herein is hexene-5-yne-1 CH$_2$=CHCH$_2$CH$_2$C≡CH.

The reactions in Steps 1 and 2 requires a catalyst to effect the reaction between the ≡SiH containing siloxanes, the mono-alkenyl polyether, and the alpha, omega-diene. Suitable catalysts are Group VIII transition metals, i.e., the noble metals. Such noble metal catalysts are described in U.S. Pat. No. 3,923,705, incorporated herein by reference. A particularly preferred catalyst is described in Karstedt's U.S. Pat. Nos. 3,715,334 and 3,814,730, incorporated herein by reference. Karstedt's catalyst is a platinum divinyl tetramethyl disiloxane complex, typically containing about one weight percent of platinum, carried in a polydimethylsiloxane fluid or in a solvent such as toluene.

The particular catalyst used in the examples was 20 μl and 200 μl portions of Karstedt's catalyst as one weight percent of platinum carried in a 2.0 mm$^2$/s polydimethylsiloxane fluid. Another preferred platinum catalyst is a reaction product of chloroplatinic acid and an organosilicon compound containing terminal aliphatic unsaturation. It is described in U.S. Pat. No. 3,419,593, incorporated herein by reference. The noble metal catalysts are used in amounts from 0.00001–0.5 parts of noble metal per 100 weight parts of ≡SiH containing polysiloxane, preferably 0.00001–0.02 parts of noble metal, most preferably 0.00001–0.002 parts of noble metal.

The mono-alkenyl polyether is a compound of the formula CH$_2$=CH(CH$_2$)$_f$O(CH$_2$CH$_2$O)$_g$(CH$_2$CH$_3$CHO)$_h$T, or a compound of the formula CH$_2$=CH—Q—O(CH$_2$CH$_2$O) $_g$(CH$_2$CH$_3$CHO)$_h$T. In the formulas, T represents an end group which can be hydrogen; a C1–C10 alkyl group such as methyl, ethyl, propyl, butyl, and decyl; an aryl group such as phenyl; or a C1–C20 acyl group such as acetyl, propionyl, butyryl, lauroyl, myristoyl, and stearoyl. Q is a divalent linking group containing unsaturation such as phenylene —C$_6$H$_4$—. The value of f is 1–6; g has a value of 4–30; and h can be zero or have a value of 1–100.

It should be noted that for vitamin A derivatives, g should have a value of at least 7, i.e. 7–30 rather than 4–30.

The term oil as used herein is intended to include compounds containing a silicon atom such as (i) low molecular weight linear and cyclic volatile methyl siloxanes, (ii) low molecular weight linear and cyclic volatile and non-volatile alkyl and aryl siloxanes, and (iii) low molecular weight functional linear and cyclic siloxanes. Most preferred, however, are low molecular weight linear and cyclic volatile methyl siloxanes (VMS). Thus, this particular component constitutes what is shown as the "oil" in Step 2 of the process illustrated above.

VMS compounds correspond to the average unit formula (CH$_3$)$_j$SiO$_{(4-j)/2}$ in which j has an average value of two to three. The compounds contain siloxane units joined by ≡Si—O—Si≡ bonds. Representative units are monofunctional "M" units (CH$_3$)$_3$SiO$_{1/2}$ and difunctional "D" units (CH$_3$)$_2$SiO$_{2/2}$.

The presence of trifunctional "T" units CH$_3$SiO$_{3/2}$ results in the formation of branched linear or cyclic volatile methyl siloxanes. The presence of tetrafunctional "Q" units SiO$_{4/2}$ results in the formation of branched linear or cyclic volatile methyl siloxanes.

Linear VMS have the formula (CH$_3$)$_3$SiO{(CH$_3$)$_2$SiO}$_k$Si (CH$_3$)$_3$. The value of k is 0–5. Cyclic VMS have the formula {(CH$_3$)$_2$SiO}$_m$. The value of m is 3–9. Preferably, these volatile methyl siloxane have a boiling point less than about 250° C. and viscosity of about 0.65 to about 5.0 mm$^2$/s.

Representative linear volatile methyl siloxanes are hexamethyldisiloxane (MM) with a boiling point of 100° C., viscosity of 0.65 mm$^2$/s, and formula Me$_3$SiOSiMe$_3$; octamethyltrisiloxane (MDM) with a boiling point of 152° C., viscosity of 1.04 mm$^2$/s, and formula Me$_3$SiOMe$_2$SiOSiMe$_3$; decamethyltetrasiloxane (MD$_2$M) with a boiling point of 194° C., viscosity of 1.53 mm$^2$/s, and formula Me$_3$SiO(Me$_2$SiO)$_2$SiMe$_3$; dodecamethylpentasiloxane (MD$_3$M) with a boiling point of 229° C., viscosity of 2.06 mm$^2$/s, and formula Me$_3$SiO(Me$_2$SiO)$_3$SiMe$_3$; tetradecamethylhexasiloxane (MD$_4$M) with a boiling point of 245° C., viscosity of 2.63 mm$^2$/s, and formula Me$_3$SiO (Me$_2$SiO)$_4$SiMe$_3$; and hexadecamethylheptasiloxane (MD$_5$M) with a boiling point of 270° C., viscosity of 3.24 mm$^2$/s, and formula Me$_3$SiO(Me$_2$SiO)$_5$SiMe$_3$.

Representative cyclic volatile methyl siloxanes are hexamethylcyclotrisiloxane (D$_3$) a solid with a boiling point of 134° C. and formula {(Me$_2$)SiO}$_3$; octamethylcyclotetrasiloxane (D$_4$) with a boiling point of 176° C., viscosity of 2.3 mm$^2$/s, and formula {(Me$_2$)SiO}$_4$; decamethylcyclopentasiloxane (D$_5$) with a boiling point of 210° C., viscosity of 3.87 mm$^2$/s, and formula {(Me$_2$)SiO}$_5$; and dodecamethylcyclohexasiloxane (D$_6$) with a boiling point of 245° C., viscosity of 6.62 mm$^2$/s, and formula {(Me$_2$)SiO}$_6$.

Representative branched volatile methyl siloxanes are heptamethyl-3-{(trimethylsilyl)oxy}trisiloxane (M$_3$T) with a boiling point of 192° C., viscosity of 1.57 mm²/s, and formula $C_{10}H_{30}O_3Si_4$; hexamethyl-3,3,bis {(trimethylsilyl)oxy}trisiloxane ($M_4Q$) with a boiling point of 222° C., viscosity of 2.86 mm²/s, and formula $C_{12}H_{36}O_4Si_5$; and pentamethyl {(trimethylsilyl)oxy}cyclotrisiloxane ($MD_3$) with the formula $C_8H_{24}O_4Si_4$.

The invention also includes using low molecular weight linear and cyclic volatile and non-volatile alkyl and aryl siloxanes represented respectively by formulas $R_3SiO(R_2SiO)_nSiR_3$ and $(R_2SiO)_p$. R can be alkyl groups with 2–20 carbon atoms or aryl groups such as phenyl. The value of n is 0–80, preferably 5–20. The value of p is 3–9, preferably 4–6. These polysiloxanes have a viscosity generally in the range of about 1–100 mm²/s.

Polysiloxanes can also be used where n has a value sufficient to provide siloxane polymers with a viscosity in the range of about 100–1,000 mm²/sec. Typically, n can be about 80–375. Illustrative of such polysiloxanes are polydimethylsiloxane, polydiethylsiloxane, polymethylethylsiloxane, polymethylphenylsiloxane, and polydiphenylsiloxane.

Low molecular weight functional polysiloxanes can also be employed, and are represented by the formula $R_3SiO(RQSiO)_nSiR_3$ where Q is a functional group. Examples of such functional polysiloxanes containing functional groups represented by Q are acrylamide functional siloxane fluids, acrylate functional siloxane fluids, amide functional siloxane fluids, amino functional siloxane fluids, carbinol functional siloxane fluids, carboxy functional siloxane fluids, chloroalkyl functional siloxane fluids, epoxy functional siloxane fluids, glycol functional siloxane fluids, ketal functional siloxane fluids, mercapto functional siloxane fluids, methyl ester functional siloxane fluids, perfluoro functional siloxane fluids, polyisobutylene (PIB) functional siloxane fluids, silanol functional siloxanes, and vinyl functional siloxane fluids.

The invention is not limited to using only low molecular weight siloxanes. Other types of oils can be used in Step 2 of the process. Thus, a oil or a mixture of oils may be used.

The term oil is therefore further intended to include (i) organic compounds, (ii) compounds containing a silicon atom as enumerated above, (iii) mixtures of organic compounds, (iv) mixtures of compounds containing a silicon atom, or (v) mixtures of organic compounds and compounds containing a silicon atom; used on an industrial scale to dissolve, suspend, or change the physical properties of other materials.

In general, the organic compounds used as oils are aromatic hydrocarbons, aliphatic hydrocarbons, alcohols, aldehydes, ketones, amines, esters, ethers, glycols, glycol ethers, alkyl halides, or aromatic halides. Representative compounds are alcohols such as methanol, ethanol, 1-propanol, cyclohexanol, benzyl alcohol, 2-octanol, ethylene glycol, propylene glycol, and glycerol; aliphatic hydrocarbons such as pentane, cyclohexane, heptane, Varnish Maker's & Painter's (VM&P) solvent, and mineral spirits; alkyl halides such as chloroform, carbon tetrachloride, perchloroethylene, ethyl chloride, and chlorobenzene; aromatic hydrocarbons such as benzene, toluene, ethylbenzene, and xylene; esters such as ethyl acetate, isopropyl acetate, ethyl acetoacetate, amyl acetate, isobutyl isobutyrate, benzyl acetate, and isopropyl palmitate; ethers such as ethyl ether, n-butyl ether, tetrahydrofuran, and 1,4-dioxane; glycol ethers such as ethylene glycol monomethyl ether, ethylene glycol monomethyl ether acetate, diethylene glycol monobutyl ether, and propylene glycol monophenyl ether; ketones such as acetone, methyl ethyl ketone, cyclohexanone, diacetone alcohol, methyl amyl ketone, and diisobutyl ketone; petroleum hydrocarbons such as petroleum jelly, mineral oil, gasoline, naphtha, kerosene, gas oil, heavy oil, and crude oil; lubricating oils such as spindle oil and turbine oil; and fatty oils such as corn oil, soybean oil, olive oil, rape seed oil, cotton seed oil, sardine oil, herring oil, and whale oil.

Other miscellaneous organic oils can also be used such as acetonitrile, nitromethane, dimethylformamide, propylene oxide, trioctyl phosphate, butyrolactone, furfural, pine oil, turpentine, and m-cresol.

Further intended to be included in the term oil are volatile flavoring agents such as oil of wintergreen; peppermint oil; spearmint oil; menthol; vanilla; cinnamon oil; clove oil; bay oil; anise oil; eucalyptus oil; thyme oil; cedar leaf oil; oil of nutmeg; oil of sage; cassia oil; cocoa; licorice; high fructose corn syrup; citrus oils such as lemon, orange, lime, and grapefruit; fruit essences such as apple, pear, peach, grape, strawberry, raspberry, cherry, plum, pineapple, and apricot; and other useful flavoring agents including aldehydes and esters such as cinnamyl acetate, cinnamaldehyde, eugenyl formate, p-methylanisole, acetaldehyde, benzaldehyde, anisic aldehyde, citral, neral, decanal, vanillin, tolyl aldehyde, 2,6-dimethyloctanal, and 2-ethyl butyraldehyde.

In addition, the term oil is intended to include volatile fragrances such as natural products and perfume oils. Some representative natural products and perfume oils are ambergris, benzoin, civet, clove, leaf oil, jasmine, mate, mimosa, musk, myrrh, orris, sandalwood oil, and vetivert oil; aroma chemicals such as amyl salicylate, amyl cinnamic aldehyde, benzyl acetate, citronellol, coumarin, geraniol, isobornyl acetate, ambrette, and terpinyl acetate; and the various classic family perfume oils such as the floral bouquet family, the oriental family, the chypre family, the woody family, the citrus family, the canoe family, the leather family, the spice family, and the herbal family.

Useful active ingredients according to this invention include both fat or oil-soluble vitamins as well as water-soluble vitamins. Oil-soluble vitamins useful herein include, but are not limited to, Vitamin $A_1$, RETINOL, $C_2$–$C_{18}$ esters of RETINOL, vitamin E, TOCOPHEROL, esters of vitamin E, and mixtures thereof. RETINOL includes trans-RETINOL, 13-cis-RETINOL, 11-cis-RETINOL, 9-cis-RETINOL, and 3,4-didehydro-RETINOL. The oil-soluble vitamin can be used in the composition according to the invention in amounts of from 0.01 to about 50 percent by weight.

RETINOL, it should be noted, is an International Nomenclature Cosmetic Ingredient Name (INCI) designated by The Cosmetic, Toiletry, and Fragrance Association (CTFA), Washington D.C., for vitamin A. Other suitable vitamins and the INCI names for the vitamins considered included herein are RETINYL ACETATE, RETINYL PALMITATE, RETINYL PROPIONATE, α-TOCOPHEROL, TOCOPHERSOLAN, TOCOPHERYL ACETATE, TOCOPHERYL LINOLEATE, TOCOPHERYL NICOTINATE, and TOCOPHERYL SUCCINATE.

Water-soluble vitamins useful herein include, but are not limited to, Vitamin C, Vitamin $B_1$, Vitamin $B_2$, Vitamin $B_6$, Vitamin $B_{12}$, niacin, folic acid, biotin, and pantothenic acid. Other suitable water-soluble vitamins and the INCI names for the vitamins considered included herein are ASCORBYL DIPALMITATE, ASCORBYL METHYLSILANOL PECTINATE, ASCORBYL PALMITATE, and ASCORBYL STEARATE. The water-soluble vitamin, like the oil-soluble vitamin, can be used in the composition according to the invention in amounts of from 0.01 to about 50 percent by weight.

Some examples of commercially available products suitable for use herein are Vitamin A Acetate and Vitamin C, both products of Fluka Chemie AG, Buchs, Switzerland; COVI-OX T-50, a vitamin E product of Henkel Corporation, La Grange, Ill.; COVI-OX T-70, another vitamin E product of Henkel Corporation, La Grange, Ill.; and vitamin E Acetate, a product of Roche Vitamins & Fine Chemicals, Nutley, N.J.

Other active ingredients may also be included in the multiple emulsion composition such as water-soluble or oil-soluble drugs. Representative examples of some suitable water-soluble drugs which can be used are hydrocortisone, ketoprofen, timolol, pilocarpine, adriamycin, mitomycin C, morphine, hydromorphone, diltiazem, theophylline, doxorubicin, daunorubicin, heparin, penicillin G, carbenicillin, cephalothin, cefoxitin, cefotaxime, 5-fluorouracil, cytarabine, 6-azauridine, 6-thioguanine, vinblastine, vincristine, bleomycin sulfate, aurothioglucose, suramin, and mebendazole.

Representative examples of some suitable oil-soluble drugs which can be used are clonidine, scopolamine, propranolol, estradiol, phenylpropanolamine hydrochloride, ouabain, atropine, haloperidol, isosorbide, nitroglycerin, ibuprofen, ubiquinones, indomethacin, prostaglandins, naproxen, salbutamol, guanabenz, labetalol, pheniramine, metrifonate, and steroids.

Not to be excluded, and considered included herein as a drug for purposes of the present invention are antiacne agents such as benzoyl peroxide, triclosan, and tretinoin; antibacterial agents such as chlorohexadiene gluconate; antifungal agents such as miconazole nitrate; anti-inflammatory agents such as salicylic acid; corticosteroidal drugs; non-steroidal anti-inflammatory agents such as diclofenac; antipsoriasis agents such as clobetasol propionate and retinoids; anesthetic agents such as lidocaine; antipruritic agents; antidermatitis agents; and agents generally considered barrier films.

The process is carried out stepwise by combining the $\equiv$SiH containing siloxane(s), the mono-alkenyl polyether, the alpha, omega-diene, the oil, and the platinum catalyst; and mixing these ingredients at room temperature until a gel, elastomer, paste, or emulsion, is formed.

If desired, the gel, elastomer, paste, or emulsion, can be made to include other active ingredients, or can be further diluted with additional similar or dissimilar oil(s), to form the final composition. A blend of hexane and tetrahydrofuran, a fragrance, or a low molecular weight siloxane, are examples of oils that could be so employed. Higher temperatures to speed up the process can be used.

If desired, all of the reactants (i.e., the $\equiv$SiH containing siloxane(s), the mono-alkenyl polyether, the unsaturated hydrocarbon, the oil, and the platinum catalyst), can be combined and reacted in one pot, as described in copending U.S. patent application Ser. No. 08/866,993, filed Jun. 2, 1997, and assigned to the same assignee as the present application.

Additional amounts of oil can be added to the gel, i.e., Optional Step 3, and the resulting mixture is subjected to shear force to form the paste. In Step 4, shear force is again used, during or after water is added to the paste, to form the primary emulsion $W_1/O$. The application of shear force is continued in Step 5, where the primary emulsion $W_1/O$ prepared in Step 4 is formed into a $W_1/O/W_2$ multiple emulsion.

Any type of mixing and shearing equipment may be used to perform these steps such as a batch mixer, planetary mixer, single or multiple screw extruder, dynamic or static mixer, colloid mill, homogenizer, sonolator, or a combination thereof.

Step 3 of the process is an optional step, as noted above. However, if Step 3 is carried out, and an oil is included, the oil should be one of those oils described previously which possesses the ability to solubilize the active ingredeient, in the case of a vitamin. Some suitable oils which possess this ability generally include silicone and hydrocarbon based oils. In addition, the oil should satisfy the melting point and the solubility requirements necessary for end uses being contemplated.

Typically, the process, i.e., Steps 1 and 2, is carried out using approximately a 1:1 equivalent ratio of the $\equiv$Si—H in the $\equiv$Si—H containing siloxane with polyether groups and the alpha, omega-diene. It is expected that useful materials may also be prepared by carrying out the process with an excess of either the $\equiv$Si—H containing siloxane or the alpha, omega-diene, but this would be considered a less efficient use of the materials. The remainder of the composition comprises the oil, in amounts generally within the range of about 65–98 percent by weight of the composition, but preferably about 80–98 percent by weight.

The most preferred method for preparing compositions according to the invention includes the steps of (i) preparing an elastomeric silicone polyether at room temperature while mixing; (ii) if required, using an additional oil to solubilize the active ingredient in the case of a vitamin(s), by adding the vitamin(s) to the oil at room temperature while mixing; and (iii) adding the vitamin(s) containing oil slowly to the elastomeric silicone polyether at room temperature while mixing.

In particular, a multiple emulsion $W_1/O/W_2$ which is capable of housing fat and water-soluble active ingredients side by side in the inner phases of the emulsion, is prepared by (i) first producing an inner emulsion, i.e., the primary emulsion $W_1/O$, and (ii) then adding the inner or primary emulsion $W_1/O$ to the outer aqueous phase $W_2$ using a minimum amount of mixing energy.

In forming primary emulsion $W_1/O$, it is preferred to use 0.1 to 99 percent by weight of the aqueous phase $W_1$, which amount includes the weight of any water-soluble active ingredient such as a vitamin(s), which may be carried therein. The oil phase O of primary emulsion $W_1/O$ is used in an amount of about 1 to 99.9 percent by weight, which amount includes the weight of the elastomeric silicone polyether, any other oil, oil-soluble vitamin(s), or fat-soluble active ingredient included therein.

The multiple emulsion $W_1/O/W_2$ can then be prepared by simply mixing together about 0.1 to 70 percent by weight of the primary emulsion $W_1/O$, with about 30 to 99.9 percent by weight of the aqueous final continuous phase $W_2$, which latter amount includes the weight of any additional water-soluble ingredient(s) contained in the final continuous phase.

EXAMPLES

The following examples are set forth for the purpose of illustrating the invention in more detail.

Example 1

Hand & Body Lotion Containing Vitamin C

In this example, two coexisting emulsions were prepared as a final product material. One of the emulsions can be designated $O'/W_2$, while the other emulsion can be designated as the $W_1/O/W_2$ multiple emulsion of the present invention.

Part A. Preparation of One of the Oil Phases (O') 10 g of stearic acid, a product of Witco Corporation, New York, N.Y., sold under the tradename HYSTRENE FG, was weighed into a glass beaker, along with 10 g of glycerol monostearate and polyoxyethylene stearate, a nonionic surfactant sold under the tradename ARLACEL 165 by ICI Surfactants, Wilmington, Del., and 25 g of petrolatum, a semisolid petroleum jelly used as an emollient, and sold under the tradename WHITE PROTOPET by Witco Corporation, New York, N.Y. The purpose of stearic acid in this example was to act as an anionic surfactant, in addition to the nonionic surfactant ARLACEL 165, in order to emulsify petroleum jelly in the O'/W$_2$ emulsion. As these components are solid, they were placed in a hot water bath at 80° C. in order to melt. 0.5 g of a crosslinked polyacrylic acid polymer, a thickener otherwise generally known as carbomer, and sold under the tradename CARBOPOL EDT 2001, by B. F. Goodrich Company, Brecksville, Ohio, was then dispersed in the melt.

Part B. Preparation of One of the Water Phases (W$_2$)

5.0 g of triethanolamine was added to 50 g of deionized water at 70° C. The solution was mixed with a Lightning brand laboratory mixer at 200 rpm (21 rad/s). The purpose of triethanolamine in this example was to function as a neutralizing agent for the carbomer thickener, which is generally somewhat acidic in nature.

Part C. Preparation of the Primary Emulsion (W$_1$/O)

20 g of a solution containing 9% by weight of an elastomeric silicone polyether having a 1:5 ratio of (EO)$_{12}$:crosslinks in decamethylcyclopentasiloxane (D$_5$) was weighed into a glass beaker and mixed at 800 rpm (84 rad/s) using a mechanical mixer. Over a period of about 20 minutes, 156 g of a solution containing 10% by weight of vitamin C, a product of Fluka Chemie AG, Buchs, Switzerland, dispersed in water (W$_1$), was added and mixed. In this example, the elastomeric silicone polyether functions as an emulsifier for D$_5$ for forming primary emulsion W$_1$/O. The phase O in primary emulsion W$_1$/O is constituted by the combination of D$_5$ and the elastomeric silicone polyether. Vitamin C, which is water soluble, constitutes part of phase W$_1$ of primary emulsion W$_1$/O.

The emulsion O'/W$_2$ was prepared by pouring Part A into Part B, and mixing Parts A and B at 200 rpm (21 rad/s) for 5 minutes. The sample was removed from the water bath and allowed to cool to 55° C. while mixing at 200 rpm (21 rad/s). Part C was then added. The speed of the mixer was gradually increased to 500 rpm (52 rad/s) to insure adequate mixing. Mixing was continued as the sample cooled to 50° C., whereupon 1.5 g of 1,3-dimethylol-5,5-dimethyl (DMDM) hydantoin, a preservative for emulsions, sold under the trademark GLYDANT® by Lonza Incorporated, Fair Lawn, N.J., and additional deionized water lost due to evaporation, were added and mixed for 5 minutes.

The resulting material was a white lotion in emulsion form that was stable. Examination of the product by optical microscope confirmed the presence of the multiple emulsion W$_1$/O/W$_2$ in the product.

Comparative Example 1

—Hand & Body Lotion

In this example, two coexisting emulsions were prepared as a final product material. One of the emulsions can be designated O'/W$_2$, while the other emulsion can be designated as the O/W$_2$ emulsion.

Part C. Preparation of the primary emulsion (W$_1$/O)

20 g of a solution containing 9% by weight of an elastomeric silicone polyether having a 1:5 ratio of (EO)$_{12}$:crosslinks in decamethylcyclopentasiloxane (D$_5$) was weighed into a glass beaker and mixed at 800 rpm (84 rad/s) using a mechanical mixer. Over a period of about 20 minutes, 156 g of a solution containing 10% by weight of vitamin C, a product of Fluka Chemie AG, Buchs, Switzerland, dispersed in water (W$_1$), was added and mixed. In this example, the elastomeric silicone polyether functions as an emulsifier for D$_5$ for forming primary emulsion W$_1$/O. The phase O in primary emulsion W$_1$/O is constituted by the combination of D$_5$ and the elastomeric silicone polyether. Vitamin C, which is water soluble, constitutes part of phase W$_1$ of primary emulsion W$_1$/O.

The emulsion O'/W$_2$ was prepared by pouring Part A into Part B, and mixing Parts A and B at 200 rpm (21 rad/s) for 5 minutes. The sample was removed from the water bath and allowed to cool to 55° C. while mixing at 200 rpm (21 rad/s). Part C was then added. The speed of the mixer was gradually increased to 500 rpm (52 rad/s) to insure adequate mixing. Mixing was continued as the sample cooled to 50° C., whereupon 1.5 g of 1,3-dimethylol-5,5-dimethyl (DMDM) hydantoin, a preservative for emulsions, sold under the trademark GLYDANT® by Lonza Incorporated, Fair Lawn, N.J., and additional deionized water lost due to evaporation, were added and mixed for 5 minutes.

The resulting material was a white lotion in emulsion form that was stable. Examination of the product by optical microscope confirmed the presence of the multiple emulsion W$_1$/O/W$_2$ in the product.

Comparative Example 1

—Hand & Body Lotion

In this example, two coexisting emulsions were prepared as a final product material. One of the emulsions can be designated O'/W$_2$, while the other emulsion can be designated as the O/W$_2$ emulsion.

Part A. Preparation of one of the Oil Phases (O')

10 g of stearic acid (HYSTRENE FG), was weighed into a glass beaker, along with 10 g of nonionic surfactant ARLACEL 165, and 25 g of petrolatum petroleum jelly. These components were placed in a hot water bath at 80° C. in order to melt. 0.5 g of carbomer was then dispersed in the melt.

Part B. Preparation of one of the Water Phases (W$_2$)

5.0 g of triethanolamine was added to 50 g of deionized water at 70° C. The solution was mixed with a Lightning brand laboratory mixer at 200 rpm (21 rad/s).

Part C. Preparation of the other of the Oil Phases (O)

25 g of a solution containing 9% by weight of an elastomeric silicone polyether having a 1:5 ratio of (EO) 12:crosslinks in decamethylcyclopentasiloxane (D$_5$) was weighed into a glass beaker. In this example, no primary emulsion was prepared.

The emulsion O'/W$_2$ was prepared by pouring Part A into Part B, and mixing Parts A and B at 200 rpm (21 rad/s) for 5 minutes. The sample was removed from the water bath and allowed to cool to 55° C. while mixing at 200 rpm (21 rad/s). Part C was then added. The speed of the mixer was gradually increased to 500 rpm (52 rad/s) to insure adequate mixing. Mixing was continued as the sample cooled to 50° C., whereupon 1.5 g of DMDM hydantoin, a preservative for emulsions, sold under the trademark GLYDANT® by Lonza Incorporated, Fair Lawn, N.J., and additional deionized water lost due to evaporation, were added and mixed for 5 minutes.

The resulting material was a white lotion in emulsion form that was stable. Examination of the product by optical microscope confirmed that no multiple emulsion was in the product. This comparative example demonstrates the effect of not forming a primary emulsion.

Comparative Example 2

—Hand & Body Lotion Containing Vitamin A & E

In this example, two coexisting emulsions were prepared as a final product material. One of the emulsions can be designated O'/$W_2$, while the other emulsion can be designated as the O/$W_{2'}$ emulsion.

Part A. Preparation of one of the Oil Phases (O')

10 g of stearic acid (HYSTRENE FG) was weighed into a glass beaker, along with 10 g of nonionic surfactant ARLACEL 165, and 25 g of petrolatum petroleum jelly. These components were placed in a hot water bath at 80° C. in order to melt.

Part B. Preparation of one of the Water Phases ($W_2$)

50 g of a one percent by weight aqueous dispersion of carbomer thickener was weighed into another beaker along with 308.5 g of hot deionized water. This dispersion was placed in a hot water bath and mixed with a mechanical mixer at 200 rpm (21 rad/s).

Part C. Preparation of the other Water Phase ($W_{2'}$)

5.0 g of triethanolamine was added to a glass beaker along with 50 g of hot deionized water. The solution was mixed by hand with a glass stirring rod until it was uniform.

Part D. Preparation of the other of the Oil Phases (O)

50 g of a solution containing 9% by weight of an elastomeric silicone polyether having a 1:5 ratio of (EO) 12:crosslinks in decamethylcyclopentasiloxane ($D_5$), was weighed into a glass beaker, and mixed at 600 rpm (63 rad/s) using a mechanical mixer. Over a period of about 10 minutes, 9.68 g of a pre-made mixture consisting of equal parts of vitamin A acetate, a product of Fluka Chemie AG, Buchs, Switzerland, and COVI-OX T-50, a vitamin E product of Henkel Corporation, La Grange, Ill., was added to the elastomeric silicone polyether. The vitamins constituted about 16.2 percent by weight of the overall weight of this (O) phase. In this example, again, no primary emulsion was prepared.

When Part A had been uniformly melted, the emulsion O'/$W_2$ was prepared by pouring Part A into Part B, and mixing Parts A and B at 200 rpm (21 rad/s) for 5 minutes. The emulsion O'/$W_2$ was then neutralized with Part C ($W_{2'}$), and mixed for about five additional minutes. During neutralization, the speed of the mixer was gradually increased from 200 to 350 rpm (21–37 rad/s) to insure adequate mixing. The sample was removed from the hot water bath and allowed to cool to 55° C. while mixing at 350 rpm (37 rad/s). When the temperature of the sample had reached 55° C., 25 g of Part D was added. Mixing was continued, and the sample was allowed to cool to 50° C. After cooling, 1.5 g of DMDM hydantoin and additional deionized water lost due to evaporation, were added to the sample, and it was mixed for 5 minutes.

The resulting material was a smooth pale yellow lotion in emulsion form that was stable. Examination of the product by optical microscope confirmed that no multiple emulsion was formed in the product. This comparative example, again, demonstrates the effect of not forming a primary emulsion.

Example 3

—Hand & Body Lotion Containing Vitamin A & E

In this example, two coexisting emulsions were prepared as a final product material. One of the emulsions can be designated O'/$W_2$, while the other emulsion can be designated as the $W_1$/O/$W_{2'}$ multiple emulsion according to the present invention. In contrast to the preceding comparative examples, a primary emulsion was formed in this example.

Part A. Preparation of one of the Oil Phases (O')

10 g of stearic acid (HYSTRENE FG) was weighed into a glass beaker, along with 10 g of nonionic surfactant ARLACEL 165, and 25 g of petrolatum petroleum jelly. These components were placed in a hot water bath at 80° C. in order to melt.

Part B. Preparation of one of the Water Phases ($W_2$)

50 g of a one percent by weight aqueous dispersion of carbomer thickener was weighed into another beaker along with 308.5 g of hot deionized water. This dispersion was placed in a hot water bath and mixed with a mechanical mixer at 200 rpm (21 rad/s).

Part C. Preparation of the other water phase ($W_{2'}$)

5.0 g of triethanolamine was added to a glass beaker along with 50 g of hot deionized water. The solution was mixed by hand with a glass stirring rod until it was uniform.

Part D. Preparation of the Primary Emulsion $W_1$/O 20 g of a solution containing 9% by weight of an elastomeric silicone polyether having a 1:5 ratio of (EO) 12:crosslinks in decamethylcyclopentasiloxane ($D_5$), was weighed into a glass beaker, and mixed at 600 rpm (63 rad/s) using a mechanical mixer. Over a period of about 10 minutes, 3.87 g of a pre-made mixture consisting of equal parts of vitamin A acetate, a product of Fluka Chemie AG, Buchs, Switzerland, and COVI-OX T-50, a vitamin E product of Henkel Corporation, La Grange, Ill., was added to the elastomeric silicone polyether. These components constituted the oil phase (O). There was then added to this mixture of components, 23.87 g of an aqueous solution ($W_1$) containing 10 percent by weight of the humectant lactic acid. These components were mixed mechanically for 15 minutes. As pointed out in Example 1, the elastomeric silicone polyether functions as emulsifier for $D_5$ for forming the primary emulsion $W_1$/O. The phase O in primary emulsion $W_1$/O is constituted by the combination of the vitamins, $D_5$, and the elastomeric silicone polyether.

When Part A had been uniformly melted, the emulsion O'/$W_2$ was prepared by pouring Part A into Part B, and mixing Parts A and B at 200 rpm (21 rad/s) for 5 minutes. The emulsion O'/$W_2$ was then neutralized with Part C ($W_{2'}$), and mixed for about five additional minutes. During neutralization, the speed of the mixer was gradually increased from 200 to 350 rpm (21–37 rad/s) to insure adequate mixing. The sample was removed from the hot water bath and allowed to cool to 55° C. while mixing at 350 rpm (37 rad/s). When the temperature of the sample had reached 55° C., 25 g of Part D was added. Mixing was continued, and the sample was allowed to cool to 50° C. After cooling, 1.5 g of DMDM hydantoin and additional deionized water lost due to evaporation, were added to the sample, and it was mixed for 5 minutes.

The resulting material was a smooth pale yellow lotion in emulsion form that was stable. Examination of the product by optical microscope confirmed the presence and coexistence in the final product of the multiple emulsion $W_1$/O/$W_{2'}$. This example demonstrates the importance of forming a primary emulsion.

While elastomeric silicone polyethers prepared according to U.S. Pat. No. 5,811,487 (Sep. 22, 1998) are most preferred for use according to this invention, other types of elastomeric silicone polyethers may be employed herein, without departing from the spirit of the invention.

For example, one type of elastomeric silicone polyether which can be used is one prepared by reacting a monoalkenyl polyether with the following two types of organosilicon monomers:

$ZMe_2SiO(Me_2SiO)_r(MeHSiO)_sSiMe_2Z$ and
$QMe_2SiO(Me_2SiO)_t(MeQSiO)_uSiMe_2Q$
where Me is methyl; Z is $CH_3$ or H provided there are at least two H atoms per molecule; Q is vinyl or another alpha-unsaturated alkenyl group or $CH_3$ provided there are at least two carbon—carbon double bonds per molecule; r is 0–1,000; s is 0–100; t is 0–1,000; and u is 0–100

Another type of elastomeric silicone polyether which can be used includes those types prepared by reacting the mono-alkenyl polyether with the following two other types of organosilicon monomers:
$(RMe_2SiO_{1/2})_v(SiO_{4/2})_w(RSiO_{3/2})_x(RMeSiO_{2/2})_y$ and
$QMe_2SiO(Me_2SiO)_z(MeQSiO)_\lambda SiMe_2Q$
where Me is methyl; R is methyl or H provided there are at least two H atoms per molecule; Q is vinyl or another alpha-unsaturated alkenyl group or methyl provided there are at least two carbon—carbon double bonds per molecule; v is 2–50; w is 0–20; x is 0–50; y is 0–1,000; z is 0–1,000; and $\lambda$ is 0–100.

Example 4 below shows a process for making this latter type of elastomeric silicone polyether.

Example 4

In this example, an ESCO EL-1 processor mixer was employed. The processor mixer was equipped with a one liter jacketed glass container having a heating and a cooling capability, an anchor sweep blade with speed control settings of 20–300 rpm (2–31 rad/s), a high speed homogenizer with Cowles type blades and speed controls for 750–15,000 rpm (78–1,570 rad/s) operations, a temperature gauge, a product inlet, a vacuum connection, and a circulation bath with a heating and a cooling capacity. The raw materials and amounts used for preparing the elastomeric silicone polyethers were 0.09 percent by weight of tetrakis (dimethylsiloxy)silane of the formula $Si[OSi(CH_3)_2H]_4$; 9.75 percent by weight of a vinyl terminated polydimethylsiloxane with approximately 300 dimethylsiloxy units in the molecule; 0.16 percent by weight of a mono-alkenyl polyether of the type $CH_2=CH(CH_2)_fO(CH_2CH_2O)_g(CH_2CH_3CHO)_hT$ where T was H; 90 percent by weight of decamethylcyclopentasiloxane; and 0.19 percent by weight of Karstedt's catalyst, a platinum divinyl tetramethyl disiloxane complex containing about one weight percent of platinum. The first step in the manufacture of the elastomeric silicone polyether was to add to the ESCO mixer tetrakis (dimethylsiloxy)silane, the mono-alkenyl polyether, and about 80 percent by weight of decamethylcyclopentasiloxane. After loading the materials into the ESCO mixer, the mixer was closed. Heating of the mixer was initiated by setting the circulatory bath set point to 50° C. The sweep blade of the mixer was activated to about 20 percent of its capacity, and the homogenizer of the mixer was activated to about 5 percent of its capacity. The platinum catalyst was added to the ESCO mixer by means of a syringe through a port hole in the mixer, and the timer was started. Mixing was continued for about one hour. The vinyl terminated polydimethylsiloxane was weighed into a beaker. It was added to the ESCO mixer by removing the inlet plug. This addition was followed by addition to the ESCO mixer of the remainder of the decamethylcyclopentasiloxane. The inlet was closed and the timer was restarted. The speed of the homogenizer was increased to about 10 percent of its capacity. The fluid in the mixer began to thicken and gel, and it began to move up the mixer shaft. Mixing was continued but the speed of the homogenizer was increased to 20–25 percent of its capacity, and the scraper in the mixer was set at 20–25 percent of its capacity. The total of the mix time measured from the point of addition of the vinyl terminated polydimethylsiloxane was about 2.5 to 3 hours at 50° C. After the elapse of that time, the mixer set point was lowered to about 25° C., and mixing was continued until the product had cooled to about 30° C. The mixer was then stopped, and the sample in the mixer was removed. The following additional example demonstrates another successful preparation of a multiple emulsion according to this invention, using an elastomeric silicone polyether of the type prepared in this example.

Example 5

Hand & Body Lotion Containing Vitamin A & E

In this example, two coexisting emulsions were prepared as a final product material. One of the emulsions can be designated $O'/W_2$, while the other emulsion can be designated as the $W_1/O/W_{2'}$ multiple emulsion according to the present invention. Again, a primary emulsion was formed in this example.

Part A. Preparation of One of the Oil Phases (O').

10 g of stearic acid (HYSTRENE FG) was weighed into a glass beaker, along with 10 g of nonionic surfactant ARLACEL 165, and 25 g of petrolatum petroleum jelly. These components were placed in a hot water bath at 80° C. in order to melt.

Part B. Preparation of One of the Water Phases ($W_2$)

50 g of a one percent by weight aqueous dispersion of carbomer thickener was weighed into another beaker along with 308.5 g of hot deionized water. This dispersion was placed in a hot water bath and mixed with a mechanical mixer at 200 rpm (21 rad/s).

Part C. Preparation of the other Water Phase ($W_{2'}$)

5.0 g of triethanolamine was added to a glass beaker along with 50 g of hot deionized water. The solution was mixed by hand with a glass stirring rod until it was uniform.

Part D. Preparation of the Primary Emulsion $W_1/O$ 70 g of a solution containing the elastomeric silicone polyether prepared in Example 4 in decamethylcyclopentasiloxane ($D_5$), was weighed into a glass beaker, and mixed at 600 rpm (63 rad/s) using a mechanical mixer. Over a period of about 10 minutes, 30 g of an aqueous solution ($W_1$) containing 10 percent by weight of vitamin C, a product of Fluka Chemie AG, Buchs, Switzerland, was added and mixed with the other two components. The elastomeric silicone polyether and decamethylcyclopentasiloxane constituted the oil phase (O). The elastomeric silicone polyether again functioned as an emulsifier for $D_5$ for forming primary emulsion $W_1/O$. The phase $W_1$ in the primary emulsion $W_1/O$ was constituted by the aqueous solution containing vitamin C as an active ingredient.

When Part A had been uniformly melted, the emulsion $O'/W_2$ was prepared by pouring Part A into Part B, and mixing Parts A and B at 200 rpm (21 rad/s) for 5 minutes. The emulsion $O'/W_2$ was then neutralized with Part C ($W_{2'}$), and mixed for about five additional minutes. During neutralization, the speed of the mixer was gradually increased from 200 to 350 rpm (21–37 rad/s) to insure adequate mixing. The sample was removed from the hot water bath and allowed to cool to 55° C. while mixing at 350 rpm (37 rad/s). When the temperature of the sample had reached 55° C., 25 g of Part D was added. Mixing was continued, and the sample was allowed to cool to 50° C. After cooling, 1.5 g of DMDM hydantoin and additional deionized water lost due to evaporation, were added to the sample, and it was mixed for 5 minutes.

The resulting material was a white lotion in emulsion form that was stable. Examination of the product by optical microscope confirmed the presence and coexistence in the final product of the multiple emulsion $W_1/O/W_2$. This example confirms the importance of forming the primary emulsion.

The compositions according to this invention have particular value in the personal care arena. They can be used alone, or blended with other cosmetic ingredients, to form a variety of over-the-counter (OTC) personal care products.

Thus, they are useful as carriers in antiperspirants and deodorants. They are lubricious and can improve the properties of skin creams, skin care lotions, moisturizers, facial treatments such as acne or wrinkle removers, personal and facial cleansers, bath oils, perfumes, colognes, sachets, sunscreens, pre-shave and after-shave lotions, liquid soaps, shaving soaps, and shaving lathers. They can be used in hair shampoos, hair conditioners, hair sprays, mousses, permanents, depilatories, and cuticle coats, to enhance gloss, and provide conditioning benefits.

In cosmetics, they can function as leveling and spreading agents for pigments in make-ups, color cosmetics, foundations, blushes, lipsticks, lip balms, eyeliners, mascaras, oil removers, color cosmetic removers, and powders. When incorporated into sticks, gels, lotions, aerosols, and roll-ons, the compositions can impart a dry, silky-smooth, payout.

In addition, the compositions exhibit other advantageous and beneficial properties such as shelf stability and ease of preparation. Hence, they can have wide application, but especially in antiperspirants, deodorants, skin care products, and for conditioning hair.

In addition, the compositions are capable of functioning as carriers for pharmaceuticals, biocides, herbicides, pesticides, and other biologically active substances; and they can be used to incorporate various water and water-soluble substances into hydrophobic systems.

Other variations may be made in compounds, compositions, and methods described herein without departing from the essential features of the invention. The embodiments of the invention specifically illustrated herein are exemplary only and not intended as limitations on their scope except as defined in the appended claims.

We claim:

1. A method of making a multiple emulsion of the type $W_1/O/W_2$ comprising first preparing a primary emulsion $W_1/O$ using a silicone fluid as the oil phase (O) and an elastomeric silicone polyether as an emulsifier for dispersing the water phase $W_1$ into the oil phase (O), and then adding and dispersing the primary emulsion $W_1/O$ into a final continuous water phase $W_2$ to form the multiple emulsion $W_1/O/W_2$.

2. A method of making a multiple emulsion of the type $W_1/O/W_2$ comprising first preparing a primary emulsion $W_1/O$ using an elastomeric silicone polyether as an emulsifier for dispersing the water phase $W_1$ into the oil phase (O), and then adding and dispersing the primary emulsion $W_1/O$ into a final continuous water phase $W_2$ to form the multiple emulsion $W_1/O/W_2$; the emulsifier being a silicone elastomer prepared by a method comprising reacting:

(A) an $\equiv$Si—H containing polysiloxane of the formula $R_3SiO(R'_2SiO)_a(R"HSiO)_bSiR_3$ or the formula $(R'_2SiO)_a(R"HSiO)_b$, and optionally an $\equiv$Si—H containing polysiloxane of the formula $HR_2SiO(R'_2SiO)_cSiR_2H$ or an $\equiv$Si—H containing polysiloxane of the formula $HR_2SiO(R'_2SiO)_a(R"HSiO)_bSiR_2H$, where R, R', and R" are alkyl groups with 1–6 carbon atoms, a is 0–250, b is 1–250, and c is 0–250; and (B) a mono-alkenyl polyether of the formula $CH_2$=CH$(CH_2)_fO(CH_2CH_2O)_g(CH_2CH_3CHO)_hT$, or the formula $CH_2$=CH—Q—O$(CH_2CH_2O)_g(CH_2CH_3CHO)_hT$, where T is hydrogen, a $C_1$–$C_{10}$ alkyl group, an aryl group, or a $C_1$–$C_{20}$ acyl group; Q is a divalent linking group containing unsaturation; f is 1–6, g is 4–30; and h is zero or 1–100; in the presence of a platinum catalyst, until an $\equiv$Si—H containing polysiloxane with polyether groups is formed;

and reacting:

(C) the $\equiv$Si—H containing polysiloxane with polyether groups; and (D) an unsaturated hydrocarbon selected from the group consisting of alpha, omega-dienes of the formula $CH_2$=CH$(CH_2)_d$CH=$CH_2$, alpha, omega-diynes of the formula CH$\equiv$C$(CH_2)_e$C$\equiv$CH, and alpha, omega-ene-ynes of the formula $CH_2$=CH$(CH_2)_e$C$\equiv$CH, where d is 1–20 and e is 0–20; in the presence of (E) an oil selected from the group consisting of (i) organic compounds, (ii) compounds containing a silicon atom, (iii) mixtures of organic compounds, (iv) mixtures of compounds containing a silicon atom, and (v) mixtures of organic compounds and compounds containing a silicon atom; and in the presence of a platinum catalyst, until a silicone elastomer is formed by crosslinking and addition of $\equiv$SiH across double or triple bonds in the unsaturated hydrocarbon.

3. A method according to claim 1 in which the oil phase is a linear volatile methyl siloxane of the formula $(CH_3)_3SiO\{(CH_3)_2SiO\}_kSi(CH_3)_3$ where k is 0–5, or a cyclic volatile methyl siloxane of the formula $\{(CH_3)_2SiO\}_m$ where m is 3–8, the volatile methyl siloxane have a boiling point less than about 250° C. and a viscosity of 0.65–5.0 $mm^2/s$.

4. A method according to claim 1 in which an oil-soluble active ingredient is included in the oil phase (O).

5. A method according to claim 1 in which a water-soluble active ingredient is included in one of water phases $W_1$ or $W_2$.

6. A method of treating hair, skin, or underarm comprising applying to the hair, skin, or underarm, the multiple emulsion prepared according to the method defined in claim 2.

7. A multiple emulsion prepared according to the method defined in claim 1.

8. A multiple emulsion prepared according to the method defined in claim 2.

9. A composition comprising a multiple emulsion of the type $W_1/O/W_2$, which multiple emulsion comprises a primary emulsion $W_1/O$ including a silicone fluid as the oil phase (O) of the primary emulsion, an elastomeric silicone polyether as the emulsifier for dispersing the water phase $W_1$ of the primary emulsion into the oil phase (O) forming the primary emulsion, and a final continuous water phase $W_2$, containing, and in which is dispersed, the primary emulsion $W_1/O$, to form the multiple emulsion $W_1/O/W_2$.

10. A composition comprising a multiple emulsion of the type $W_1/O/W_2$, which multiple emulsion comprises a primary emulsion $W_1/O$ including as the oil phase (O) of the primary emulsion, an oil selected from the group consisting of (i) organic compounds, (ii) compounds containing a silicon atom, (iii) mixtures of organic compounds, (iv) mixtures of compounds containing a silicon atom, and (v) mixtures of organic compounds and compounds containing a silicon atom; an elastomeric silicone polyether as the emulsifier for dispersing the water phase $W_1$ of the primary emulsion into the oil phase (O) for forming the primary emulsion; and a final continuous water phase $W_2$, containing, and in which is dispersed, the primary emulsion $W_1/O$, for forming the multiple emulsion $W_1/O/W_2$; the emulsifier being a silicone elastomer prepared by a method comprising reacting:

(A) an ≡Si—H containing polysiloxane of the formula $R_3SiO(R'_2SiO)_a(R''HSiO)_bSiR_3$ or the formula $(R'_2SiO)_a(R''HSiO)_b$, and optionally an ≡Si—H containing polysiloxane of the formula $HR_2SiO(R'_2SiO)_cSiR_2H$ or an ≡Si—H containing polysiloxane of the formula $HR_2SiO(R'_2SiO)_a(R''HSiO)_bSiR_2H$, where R, R', and R" are alkyl groups with 1–6 carbon atoms, a is 0–250, b is 1–250, and c is 0–250; and (B) a mono-alkenyl polyether of the formula $CH_2=CH(CH_2)_fO(CH_2CH_2O)_g(CH_2CH_3CHO)_hT$, or the formula $CH_2=CH—Q—O(CH_2CH_2O)_g(CH_2CH_3CHO)_hT$, where T is hydrogen, a $C_1$–$C_{10}$ alkyl group, an aryl group, or a $C_1$–$C_{20}$ acyl group; Q is a divalent linking group containing unsaturation; f is 1–6, g is 4–30; and h is zero or 1–100; in the presence of a platinum catalyst, until an ≡Si—H containing polysiloxane with polyether groups is formed;

and reacting:

(C) the ≡Si—H containing polysiloxane with polyether groups; and (D) an unsaturated hydrocarbon selected from the group consisting of alpha, omega-dienes of the formula $CH_2=CH(CH_2)_dCH=CH_2$, alpha, omega-diynes of the formula $CH≡C(CH_2)_eC≡CH$, and alpha, omega-ene-ynes of the formula $CH_2=CH(CH_2)_eC≡CH$, where d is 1–20 and e is 0–20; in the presence of (E) an oil selected from the group consisting of (i) organic compounds, (ii) compounds containing a silicon atom, (iii) mixtures of organic compounds, (iv) mixtures of compounds containing a silicon atom, and (v) mixtures of organic compounds and compounds containing a silicon atom; and in the presence of a platinum catalyst, until a silicone elastomer is formed by crosslinking and addition of ≡SiH across double or triple bonds in the unsaturated hydrocarbon.

* * * * *

UNITED STATES PATENT AND TRADEMARK OFFICE
CERTIFICATE OF CORRECTION

PATENT NO. : 5,948,855

DATED : September 7, 1999

INVENTOR(S) : Zuchen Lin, William James Schulz Jr., Shizhong Zhang

It is certified that error appears in the above-identified patent and that said Letters Patent is hereby corrected as shown below:

Column 9, line 55, the heading of the Example should read:
--- Example 2 ---

Signed and Sealed this

Fourteenth Day of March, 2000

*Attest:*

Q. TODD DICKINSON

*Attesting Officer*  *Commissioner of Patents and Trademarks*